US00PP37445P3

(12) United States Plant Patent
Raymer et al.

(10) Patent No.: US PP37,445 P3
(45) Date of Patent: May 26, 2026

(54) **SEASHORE *PASPALUM* PLANT NAMED 'UGP 73'**

(50) Latin Name: ***Paspalum vaginatum* Swartz**
Varietal Denomination: UGP 73

(71) Applicant: University of Georgia Research Foundation, Inc., Athens, GA (US)

(72) Inventors: Paul Raymer, Milner, GA (US); Brian Schwartz, Tifton, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 19/181,402

(22) Filed: Apr. 17, 2025

(65) Prior Publication Data

US 2025/0338783 P1 Oct. 30, 2025

Related U.S. Application Data

(60) Provisional application No. 63/731,363, filed on Apr. 24, 2024.

(51) Int. Cl.
*A01H 5/00* (2018.01)
*A01H 6/46* (2018.01)

(52) U.S. Cl.
USPC ..... Plt./388
CPC ..... *A01H 6/46* (2018.05); *A01H 5/00* (2013.01)

(58) Field of Classification Search
USPC ..... Plt./384, 388
CPC ..... A01H 6/4648; A01H 5/00
See application file for complete search history.

*Primary Examiner* — Keith O. Robinson
(74) *Attorney, Agent, or Firm* — Thomas|Horstemeyer, LLP

(57) ABSTRACT

A new and distinct cultivar of Seashore *Paspalum* plant, botanically known as *Paspalum vaginatum* Swartz, named 'UGP 73', characterized by its excellent turf quality, excellent turf color, superior drought tolerance, and superior salt tolerance.

6 Drawing Sheets

Genus and species: Latin name: *Paspalum vaginatum* Swartz.

Variety denomination: Variety denomination: The new *Paspalum vaginatum* Swartz claimed is of the cultivar denominated 'UGP 73'.

BACKGROUND OF THE INVENTION

The present invention relates to a new and distinct cultivar of Seashore *Paspalum* plant, botanically known as *Paspalum vaginatum* Swartz, and hereinafter referred to by the cultivar name 'UGP 73'.

'UGP 73' is a vegetative clone developed from a single $F_1$ seed arising from the hand-pollinated cross ('Durban' (PI 614678; not patented) X experimental line 'G05-1743' (not patented)). This cross was made in the greenhouse at Griffin, Georgia in 2007 by Dr. Paul Raymer. The female parent, 'Durban' (not patented), was collected in Durban, South Africa.

'UGP 73' is a vigorous vegetative seashore *Paspalum* cultivar that produces excellent quality turf under a range of mowing heights, and is suitable for use on golf courses, athletic fields, and other recreational venues as fine turf. 'UGP 73' has been under development and evaluation for 16 years. 'UGP 73' has been evaluated extensively in both in the National Turfgrass Evaluation Program (NTEP) at eight southern locations from 2016-2020 and as part of a USDA Specialty Crops Research Grant (SCRI) at six southern locations from 2011-2013 and in SCRI advanced trials at six locations in 2016-2019. In the two-year SCRI trial, 'UGP 73' ranked $2^{nd}$ in overall turf quality out of 80 entries and ranked 1st in turf quality under non-drought conditions.

BRIEF SUMMARY OF THE INVENTION

The new *Paspalum vaginatum* Swartz cultivar 'UGP 73' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Paspalum* cultivar named 'UGP 73'. In combination, these traits set 'UGP 73' apart from all other existing varieties of *Paspalum* known to the inventors:

1. 'UGP 73' has excellent turf quality over a wide range of mowing heights and has often outperformed Salam™ (not patented), 'Sealsle 1' (U.S. Plant Pat. No. 12,665), SeaStar® (U.S. Plant Pat. No. 25,761), Platinum TE® (U.S. Plant Pat. No. 19,224), and SeaDwarf™ (U.S. Plant Pat. No. 13,294) (Tables 1, 7, 11, and 12).
2. 'UGP 73' has excellent turf color, often better than Salam™ (not patented), 'Sealsle 1' (U.S. Plant Pat. No. 12,665), SeaStar® (U.S. Plant Pat. No. 25,761), Platinum TE® (U.S. Plant Pat. No. 19,224), and SeaDwarf™ (U.S. Plant Pat. No. 13,294) (Tables 2, 5, 11, and 12).
3. 'UGP 73' has demonstrated superior drought tolerance to SeaStar® (U.S. Plant Pat. No. 25,761) over a wide range of irrigation regimes (Table 7).
4. The salt tolerance of 'UGP 73' is similar to that of SeaStar® (U.S. Plant Pat. No. 25,761) and better than that of 'Sealsle 1' (U.S. Plant Pat. No. 12,665) (Table 10).

5. 'UGP 73' has demonstrated better tolerance to 60% shade than has Platinum TE® (U.S. Plant Pat. No. 19,224) and SeaStar® (U.S. Plant Pat. No. 25,761) (Table 9).

Additional characteristics of 'UGP 73' known to the inventors also include:

1. Good turf density (Table 3).
2. Acceptable retention of color and quality during the fall and winter months following light frost or cool temperatures (Tables 4 and 5).
3. Medium to fine leaf texture.
4. Good resistance to dollar spot disease, *Clarireedia* sp. (Tables 6, 11, and 12)
5. Produces acceptable quality sod with good tensile strength (Table 8).

BRIEF DESCRIPTION OF THE DRAWINGS

The accompanying colored photographic illustrations show the overall appearance and distinct characteristics of the new *Paspalum vaginatum* Swartz cultivar denominated 'UGP 73' showing the colors as true as possible. Colors in the photographs may differ slightly from the color values cited in the detailed botanical description, which accurately describes the colors of the new Genus species 'UGP 73'.

DETAILED BOTANICAL DESCRIPTION

Figure 1:
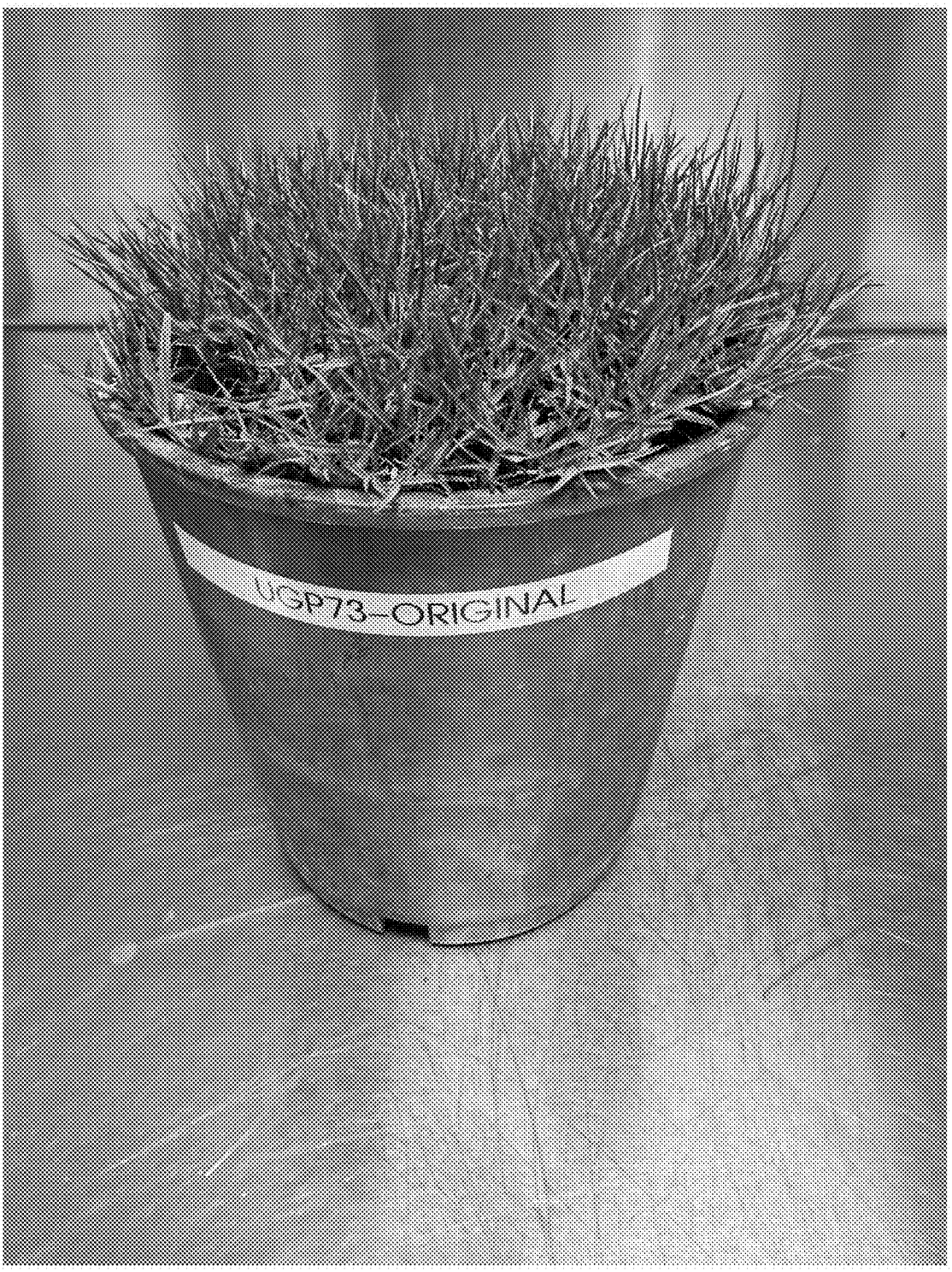
FIG. 1 shows a potted greenhouse sample of 'UGP 73' that is about 15-16 years old that has been maintained in a greenhouse by trimming and repotting to maintain vigorous growth.
Figure 2:
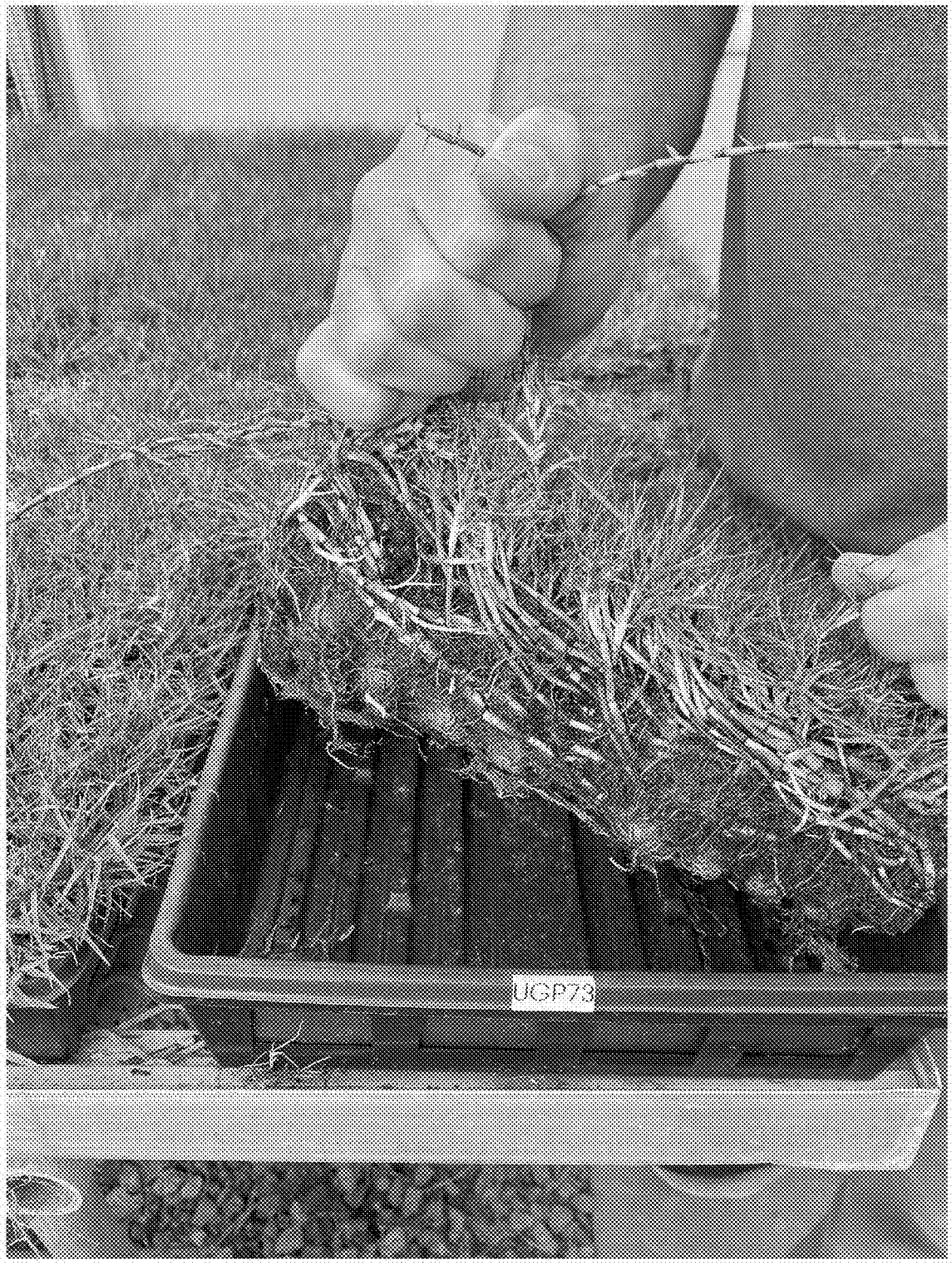
FIG. 2 shows abundance of stolons and rhizomes in a greenhouse flat of 'UGP 73'.
Figure 3:
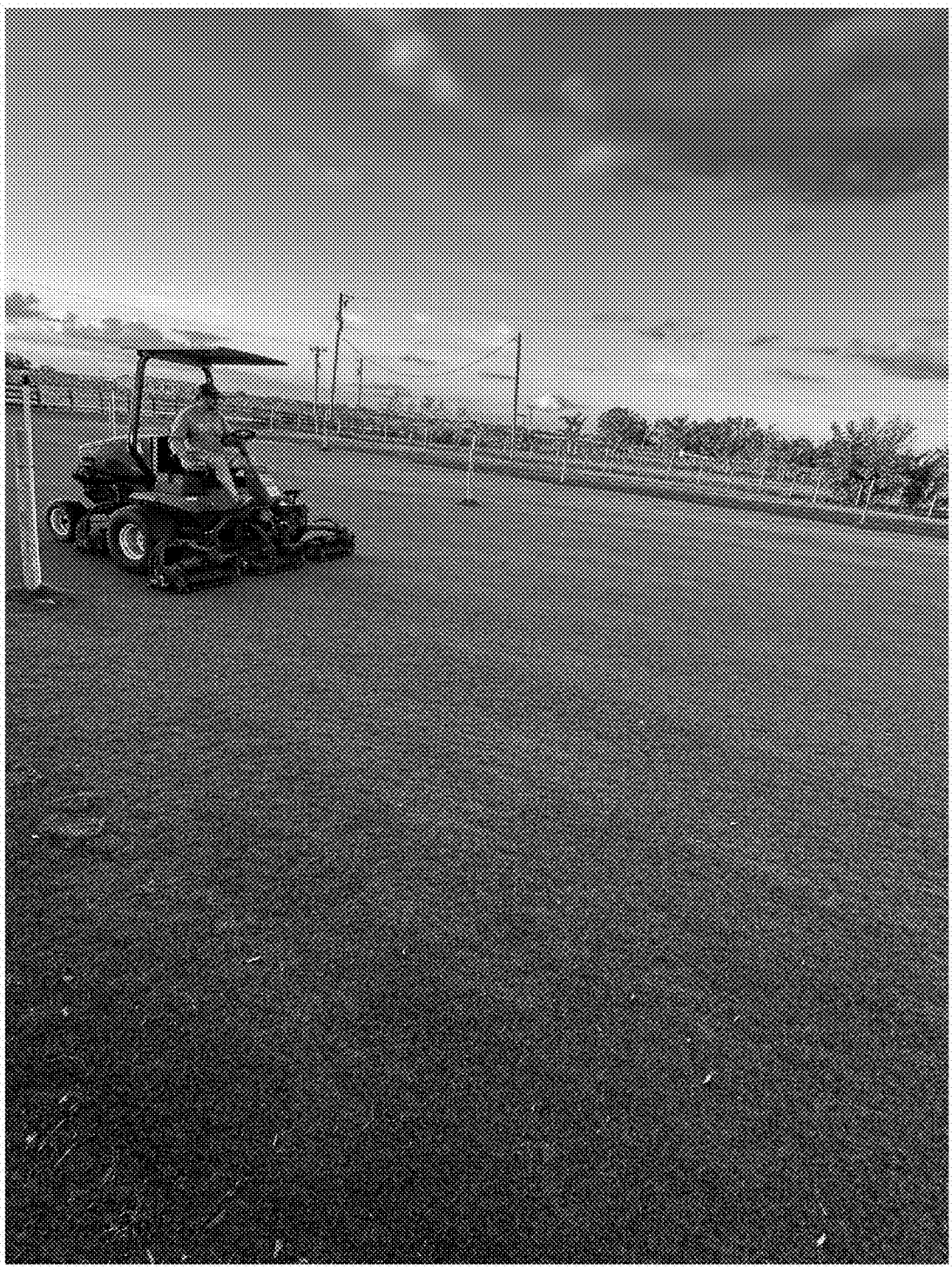
FIG. 3 shows a field of 'UGP 73' as managed turf.
Figure 4:
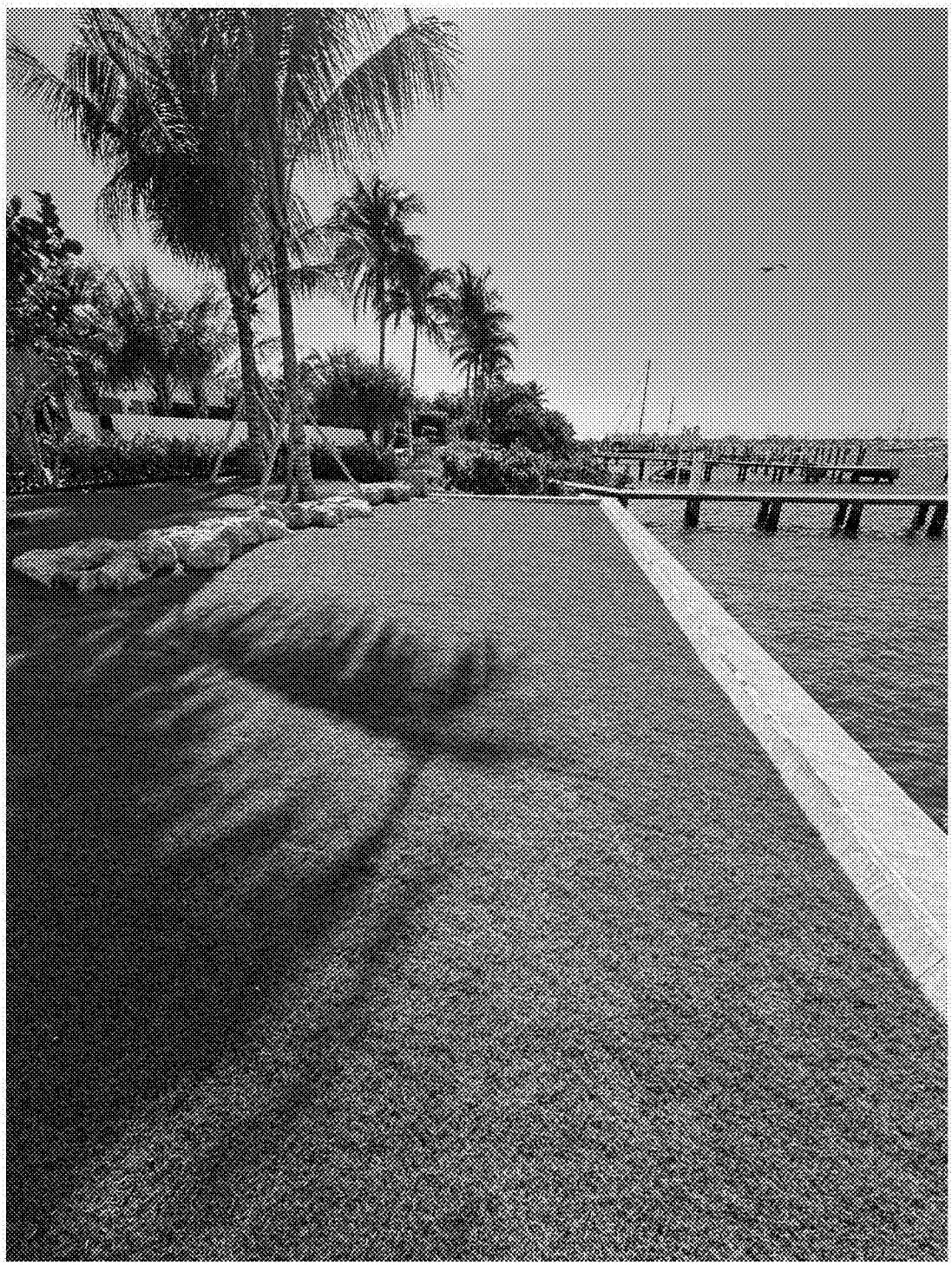
FIG. 4 shows 'UGA 73' in use on a coastal landscape.
Figure 5:
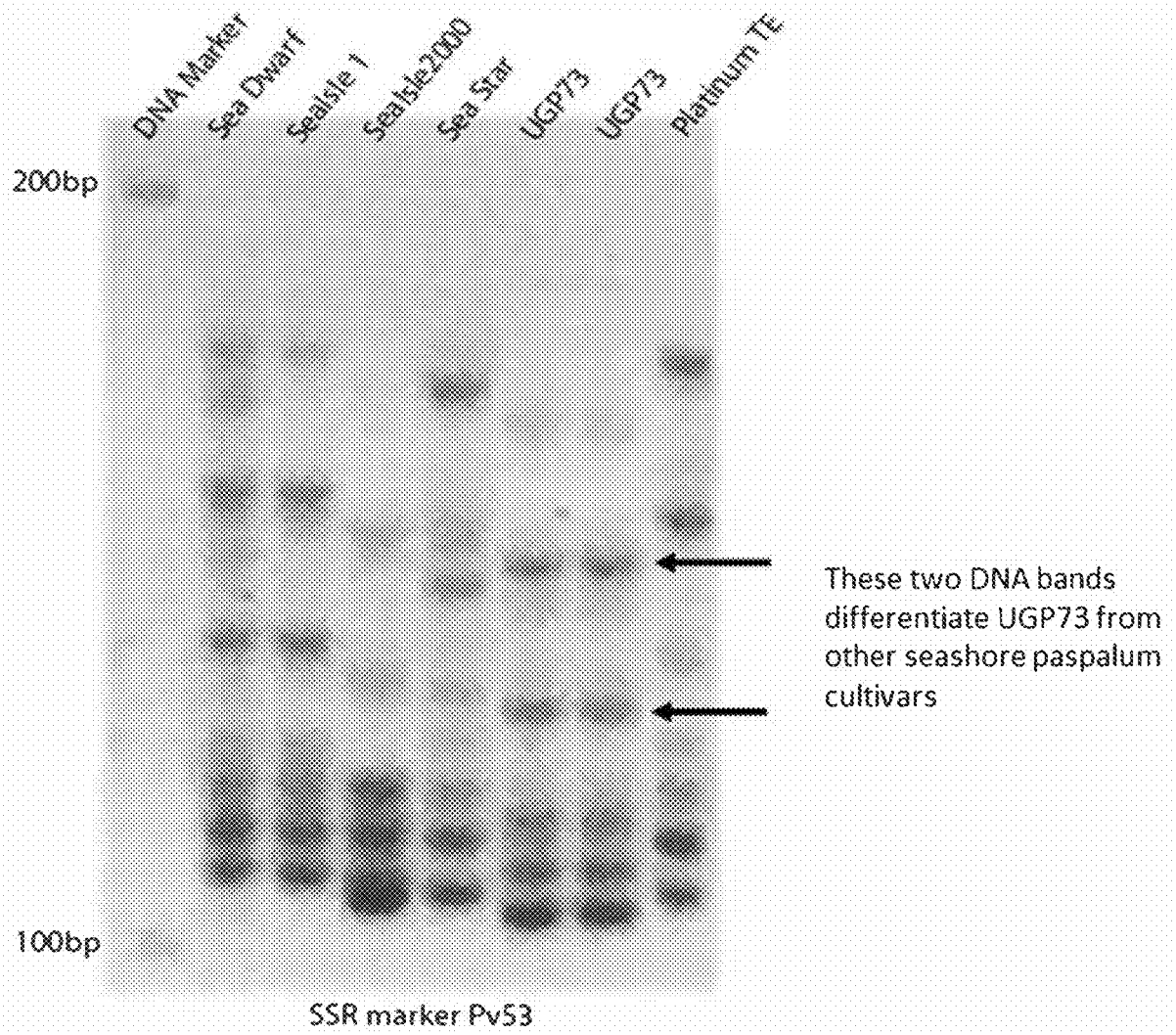
FIG. 5 compares the SSR Pv53 generated banding patterns obtained from DNA of 'UGP 73' to that from commercial cultivars.
Figure 6:
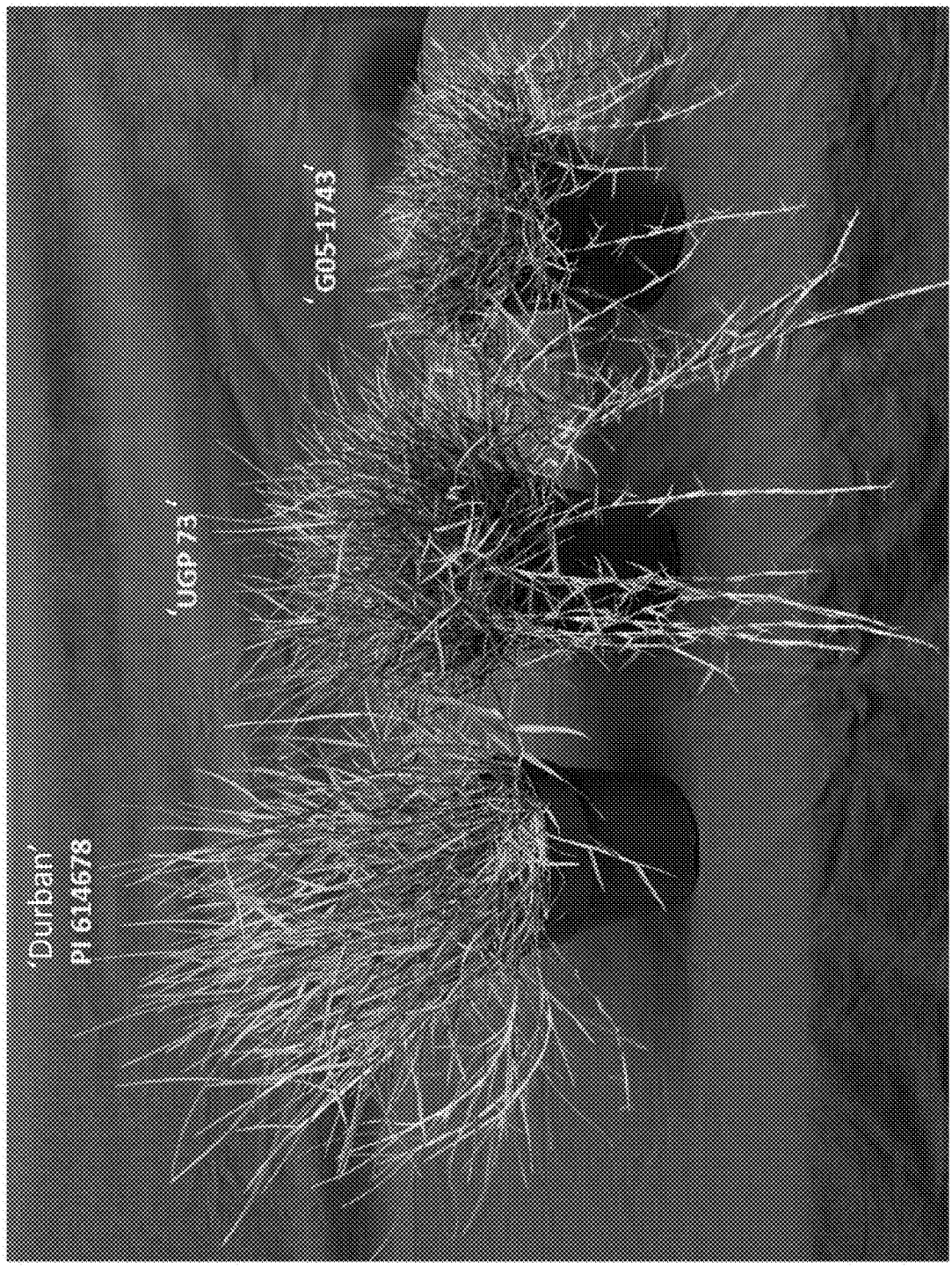
FIG. 6. Photograph showing plant characteristics of the female parent, 'Durban' (PI 614678) (left), the male parent, 'G05-1743' (right), and their F1 progeny, 'UGP 73' (center).

The following traits have been consistently observed in the original plant of this new variety grown in Griffin, Georgia, and, to the best knowledge of the inventors, their combination forms the unique characteristics of the new variety 'UGP 73'.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Paspalum vaginatum* Swartz cultivar 'UGP 73'. Data were collected from plants that were approximately eight years old and were grown in the ground under greenhouse and outdoor conditions in Griffin, GA. The average outdoor low temperatures ranged from lows of about 33° F. to 42° F. in the winter, to average high temperatures of about 85° F. to 92° F. in summer.

1. The plant: 'UGP 73' is a vigorous variety with upright growth habit. It is dense and spreads rapidly by producing large numbers of rhizomes and stolons.

The mean height of the unmown canopy (culm height) is 16.4 cm, with a seed head exsertion height above the canopy of 4.8 cm.

2. Flowering tillers: The mean length and diameter of the peduncle are respectively 9.6 mm and 0.6 mm.

The mean length of the longest spike is 23.7 mm and there are two spikes per inflorescence.

The mean length of the spike branch from the flag leaf is 8.9 mm and the length and width of the blade on the flag leaf are respectively 6.0 mm and 0.9 mm. The mean length of the sheath on the flag leaf is 33.3 mm.

The mean length and width of the blade of the 4$^{th}$ leaf (the flag leaf is the 1$^{st}$ leaf) are respectively 37.4 mm and 3.1 mm, and the mean length of the sheath on the 4$^{th}$ leaf is 14.1 mm. The mean length of the 4$^{th}$ internode is 11.3 mm. The color of the upper leaf surface is Green 137 B and the lower leaf surface color is Green 137 C.

The anther color is Violet 83 A, and stigma color is Violet 86 A. Seeds are not produced in pure monostands due to self-incompatibility.

3. Stolons: The mean length and diameter of the 4th internode from the tip are 13.8 mm and 1.6 mm respectively.

The mean length and width of the 4$^{th}$ leaf blade, at the 4$^{th}$ node on stolon, are 6.7 mm and 2.6 mm respectively, with a leaf sheath that is 8.6 mm long.

The color of the stolon is Yellow-Green 146 D.

4. Method of propagation: Vegetative (Clonal). 'UGP 73' was initially asexually reproduced in a greenhouse on in Griffin, Georgia with repeated cycles of plant propagation using vegetative sprigs and stolons followed by vegetative growth to expand the quantity of plant material
5. Pedigree and history: 'UGP 73' is a vegetative clone developed from a single $F_1$ seed arising from the hand-pollinated cross ('Durban' (PI 614678; not patented) X experimental line 'G05-1743'). This cross was made in the greenhouse at Griffin, Georgia in 2007 by Dr. Paul Raymer. The female parent, Durban, was collected in Durban, South Africa.

Originally designated as 'G07-033.4', the single plant was germinated from seed in the laboratory and was established in the greenhouse. The seedling was visually screened for acceptable turf quality prior to being transplanted into the field for initial turf evaluation in the spring of 2010. 'G07-033.4' was evaluated in un-replicated field plots (2010 single plant nursery) mowed at 1.5 inches height of cut (h.o.c.) along with approximately 2000 other seedlings beginning in June of 2010. 'G07-033.4' was one of 80 lines selected for further evaluation in the fall of 2010 based on turf superior quality, density, color, and resistance to dollar spot disease. 'G07-033.4' was clonally propagated and increased during the spring of 2011 and included in a group of 80 seashore *Paspalum* lines and re-designated as 'UGP 73' in replicated trials at seven southern field locations (Griffin, GA; Tifton, GA; College Station, TX; Dallas, TX; Raleigh, NC; Gainesville, FL; and Stillwater, OK.) for turf performance and drought tolerance as part of a USDA Specialty Crops Research Grant (SCRI). In this two-year evaluation over seven locations, 'UGP 73' ranked $2^{nd}$ in overall turf quality out of 80 entries and ranked $1^{st}$ in turf quality under non-drought conditions (data not presented).

In 2015, 'UGP 73' was increased clonally in the greenhouse for inclusion in the National Turfgrass Evaluation Program (NTEP) seashore *Paspalum* trials at eight southern locations from 2016-2020. NTEP trial locations were Auburn, AL; Fayetteville, AR; Riverside, CA; Jay, FL; Griffin, GA; Mississippi State, MS; Stillwater, OK; and College Station, TX and (h.o.c.) at these locations ranged from 0.5-2.5 inches. 'UGP 73' was also included in extensive trials associated with our second federal SCRI grant (2016-2019) where it was further evaluated for drought tolerance, salt tolerance, shade tolerance, and sod strength. In 2019, 'UGP 73' one of 23 advanced breeding lines and four standard cultivars included in a "greens" trial (0.110 to 0.175 inch h.o.c.). After the failure of an advanced line fairway trial (established in 2017) on the Griffin Campus, 'UGP 73' was included as one 28 entries in an advanced fairway trial established in 2020 on the UGA Griffin campus. Foundation and Registered fields of 'UGP 73' are established at Creekside Growers, Arcadia, Florida.

6. Description of plant material: 'UGP 73' is a vigorous clonal line that produces excellent quality turf under a range of mowing heights (Tables 1, 8, 12, and 13) and is suitable for use on golf courses, athletic fields, and other recreational venues as a fine turf. 'UGP 73' has excellent turf color (Tables 2, 5, 12, and 13), good turf density (Table 3) and acceptable retention of color and quality during the fall and winter months following light frost or cool temperatures (Tables 4 and 5). In limited evaluations, 'UGP 73' has shown less winter kill than 'Sealsle 1' (U.S. Plant Pat. No. 12,665), 'SeaStar®' (U.S. Plant Pat. No. 25,761), and 'Salam™' (not patented) (Table 6). It is similar to other commercial cultivars with medium to fine leaf texture and good turf density. 'UGP 73' was initially selected for its drought tolerance and has demonstrated superior performance in numerous non-irrigated trials as well as over a wide range of irrigation regimes (Table 8). It has excellent salt tolerance, similar to SeaStar® (U.S. Plant Pat. No. 25,761) (Table 11), and better performance under shade than SeaStar® (U.S. Plant Pat. No. 25,761) and 'Platinum' (Table 10). 'UGP 73' has good resistance to dollar spot disease, *Clarireedia* sp. (Tables 7, 12, and 13) and has been shown to produce acceptable quality sod with good tensile strength (Table 9).
7. Other: Golf course developments placed on coastal venues and problems associated with salinity are increasingly more prevalent issues in managed turfgrass. The trend for use of more salt-laden irrigation waters on turfgrass sites is expected to continue to rise and to further increase interest in developing more salt-tolerant grasses, especially halophytes such as seashore *Paspalum*.

A) 'UGP 73' has excellent turf quality over a wide range of mowing heights and has often outperformed 'Salam™' (not patented), 'Sealsle 1' (U.S. Plant Pat. No. 12,665), 'SeaStar®' (U.S. Plant Pat. No. 25,761), 'Platinum TE', and SeaDwarf™ (U.S. Plant Pat. No. 13,294) (Tables 1, 8, 12, and 13).

B) 'UGP 73' has excellent genetic color often better than Salam™ (not patented), Sealsle 1 (U.S. Plant Pat. No. 12,665), SeaStar® (U.S. Plant Pat. No. 25,761), Platinum, and SeaDwarf™ (U.S. Plant Pat. No. 13,294). (Table 2, 5, 12, and 13)

C) 'UGP 73' has demonstrated superior drought tolerance to SeaStar® (U.S. Plant Pat. No. 25,761) over a wide range of irrigation regimes (Table 8).

D) The salt tolerance of 'UGP 73' is similar to that of SeaStar® (U.S. Plant Pat. No. 25,761) and better than that of Sealsle 1 (U.S. Plant Pat. No. 12,665) (Table 11).

E) 'UGP 73' has demonstrated better tolerance to 60% shade than has Platinum and SeaStar® (U.S. Plant Pat. No. 25,761) (Table 10).

TABLE 1

NTEP 2016-2020 Seashore Paspalum - Turf Quality

| NTEP Entry | 2016 (1-9)+ | 2017 (1-9) | 2018 (1-9) | 2019 (1-9) |
|---|---|---|---|---|
| Salam ™ | **6.1*** | 6.1 | 6.0 | 6.0 |
| Sea Isle 1 | **6.2** | 6.0 | **6.1** | **6.2** |
| SeaStar ® | **5.9** | 6.1 | **6.1** | **6.1** |
| 'UGP 73' | **6.3** | **6.5** | **6.2** | **6.3** |
| C.V. | 4.4 | 1.3 | 2.6 | 2.1 |
| LSD | 0.4 | 0.1 | 0.2 | 0.2 |

| NTEP Entry | 2020 (1-9) | Top Statistical Group | 5 yr. Avg (1-9) |
|---|---|---|---|
| Salam ™ | **6.2** | 2/5 | 6.1 |
| Sea Isle 1 | **5.9** | 4/5 | 6.1 |
| SeaStar ® | **6.0** | 4/5 | 6.0 |
| 'UGP 73' | **6.1** | 5/5 | 6.3 |
| C.V. | 3.0 | | |
| LSD | 0.3 | | |

+Rated on 1-9 scale with 6 = acceptable and 9 = excellent
*Means in the top statistical group are bolded.

TABLE 2

NTEP 2016-2020 Seashore Paspalum - Genetic Color

| NTEP Entry | 2016 (1-9) | 2017 (1-9) | 2018 (1-9) | 2019 (1-9) |
|---|---|---|---|---|
| Salam ™ | **5.7*** | 6.2 | 6.2 | **6.6** |
| Sea Isle 1 | **6.0** | 6.4 | 6.3 | **6.7** |
| SeaStar ® | 5.0 | 6.4 | 6.6 | 6.3 |
| 'UGP 73' | **6.0** | **6.0** | **6.9** | **6.8** |
| C.V. | 4.5 | 2.8 | 2.5 | 4.4 |
| LSD | 0.4 | 0.3 | 0.3 | 0.5 |

| NTEP Entry | 2020 (1-9) | Top Statistical Group | 5 yr. Avg (1-9) |
|---|---|---|---|
| Salam ™ | **5.9** | 3/5 | 6.1 |
| Sea Isle 1 | 5.5 | 2/5 | 6.2 |
| SeaStar ® | **6.3** | 1/5 | 6.1 |
| 'UGP 73' | **6.5** | 5/5 | 6.7 |
| C.V. | 5.7 | | |
| LSD | 0.6 | | |

*Means in the top statistical group are bolded.

TABLE 3

NTEP 2016 - 2020 Seashore Paspalum - Fall Density

| NTEP Entry | Riverside, CA (1-9) | Jay, FL (1-9) | Miss. St., MS (1-9) |
|---|---|---|---|
| Salam ™ | **6.2*** | **6.4** | **6.8** |
| Sea Isle 1 | **5.4** | **6.6** | **7.0** |
| SeaStar ® | 5.2 | **6.5** | **6.8** |
| 'UGP 73' | **5.4** | **6.8** | **7.5** |
| C.V. | 8.7 | 9.0 | 6.1 |
| LSD | 0.8 | 1.0 | 0.7 |

| NTEP Entry | Stillwater, OK (1-9) | Top Statistical Group | Table Avg. (1-9) |
|---|---|---|---|
| Salam ™ | 6.4 | **4/5** | **6.4** |
| Sea Isle 1 | 6.0 | 3/5 | 6.2 |
| SeaStar ® | 6.3 | 2/5 | 6.1 |
| 'UGP 73' | 6.2 | **4/5** | **6.4** |
| C.V. | 2.9 | | 3.9 |
| LSD | 0.3 | | 0.4 |

*Means in the top statistical group are bolded.

TABLE 4

NTEP 2016-2020 Seashore Paspalum - Winter Quality

| NTEP Entry | 2016 (1-9) | 2017 (1-9) | 2018 (1-9) | 2019 (1-9) |
|---|---|---|---|---|
| Salam ™ | **6.0** | **6.1** | **5.7** | **5.9** |
| Sea Isle 1 | **5.3** | **5.7** | **6.0** | **6.1** |
| SeaStar ® | **5.7** | **5.8** | **5.9** | **6.0** |
| 'UGP 73' | **5.7** | **5.8** | **5.8** | **5.9** |
| C.V. | 11.7 | 7.9 | 4.9 | 3.4 |
| LSD | 1.0 | 0.7 | 0.5 | 0.3 |

| NTEP Entry | 2020 (1-9) | Top Statistical Group | 5 yr. Avg (1-9) |
|---|---|---|---|
| Salam ™ | **6.1** | 5/5 | 5.9 |
| Sea Isle 1 | **5.3** | 5/5 | 5.7 |
| SeaStar ® | 4.8 | 4/5 | 5.6 |
| 'UGP 73' | 5.1 | 4/5 | 5.6 |
| C.V. | 10.1 | | |
| LSD | 0.9 | | |

*Means in the top statistical group are bolded.

TABLE 5

NTEP 2016-2020 Seashore Paspalum - Color October

| NTEP Entry | Auburn, AL (1-9) | Jay, FL (1-9) | Griffin, GA (1-9) |
|---|---|---|---|
| Salam ™ | 5.9 | 6.3 | **6.2** |
| Sea Isle 1 | 5.8 | 6.1 | **6.3** |
| SeaStar ® | **6.1** | 5.9 | **6.2** |
| 'UGP 73' | **6.5** | **7.0** | **6.2** |
| C.V. | 7.6 | 7.0 | 6.0 |
| LSD | 0.7 | 0.7 | 0.6 |

| NTEP Entry | Stillwater, OK (1-9) | Top Statistical Group | Table Avg. (1-9) |
|---|---|---|---|
| Salam ™ | 6.2 | 1/4 | 6.2 |
| Sea Isle 1 | 6.0 | 1/4 | 6.1 |

TABLE 5-continued

NTEP 2016-2020 Seashore Paspalum - Color October

| | | | |
|---|---|---|---|
| SeaStar ® | 5.7 | 2/4 | 6.0 |
| 'UGP 73' | 6.5 | **3/4** | **6.5** |
| C.V. | 4.1 | | 3.7 |
| LSD | 0.4 | | 0.4 |

*Means in the top statistical group are bolded.

TABLE 6

NTEP 2016-2020 Seashore Paspalum - Winter Kill

| NTEP Entry | Fayetteville, AR (% winter kill) |
|---|---|
| Salam ™ | 22.5 |
| Sea Isle 1 | 20.8 |
| SeaStar ® | 56.7 |
| 'UGP 73' | **9.2** |
| C.V. | 22.0 |
| LSD | 11.6 |

*Means in the top statistical group are bolded.

TABLE 7

NTEP 2016-2022 Seashore Paspalum - Dollar Spot Disease

| NTEP Entry | Auburn, AL (1-9) | Jay, FL (1-9) | Miss. St., MS (1-9) | Table Avg. (1-9) |
|---|---|---|---|---|
| Salam ™ | 2.0 | 4.3 | **7.0** | **4.8** |
| Sea Isle 1 | 2.7 | **7.0** | **7.3** | **5.7** |
| SeaStar ® | **5.3*** | **8.3** | 4.7 | **6.1** |
| 'UGP 73' | **6.0** | 5.0 | **6.3** | **5.8** |
| C.V. | 55.4 | 23.9 | 19.4 | 18.7 |
| LSD | 4.2 | 2.6 | 1.8 | 1.7 |

*Means in the top statistical group are bolded

TABLE 8

SCRI Seashore Paspalum Drought Trials - 2017 - College Station, Texas

| SCRI | Turf Quality (1-9) Irrigation Frequency (times / month) | | | | |
|---|---|---|---|---|---|
| Entry | 0 | 1 | 2 | 4 | 8 |
| SeaStar ® | 5.49 | 6.22 | 6.14 | 6.93 | 6.84 |
| SR31-15-15 | 5.03 | 6.04 | 5.99 | 6.64 | 6.60 |
| 'UGP 144' | 5.58 | 6.24 | 6.30 | 6.89 | 6.77 |
| 'UGP 73' | 5.63 | 6.31 | 6.44 | 7.01 | 6.93 |

| SCRI Entry | Average | Rank |
|---|---|---|
| SeaStar ® | 6.32 | 3 |
| SR31-15-15 | 6.06 | 4 |
| 'UGP 144' | 6.35 | 2 |
| 'UGP 73' | 6.46 | 1 |

TABLE 9

Sod Handling Quality and Tensile Strength of Seashore Paspalum Oklahoma State University - 2017

| Entry | Mean SHQ[1] (1-5) | STS[2] 14 MAP (kg/dm) | STS[2] 18 MAP (kg/dm) | Mean STS[2] (kg/dm) |
|---|---|---|---|---|
| Salam ™ | **4.2*** | **115.9** | 70.9 | 93.4 |
| SeaIsle 1 | **4.3** | **106.6** | 68.3 | 87.4 |
| SeaStar ® | **4.2** | **104.3** | 53.1 | 87.0 |
| 'UGP 73' | **4.2** | 89.6 | **105.1** | **97.1** |
| Test Average (10 entries) | 3.5 | 95.6 | 66.4 | 81.0 |

[1]Sod handling quality rated on 1-5 scale with 3 = minimum acceptable and 5 = excellent.
[2]Sod tensile strength in kg $dm^{-2}$ recorded at the peak force required to cause sod pad tearing using a hand winch and force transducer/recorder.
*Means in the top statistical group are bolded.

TABLE 10

SCRI III Shade Trial - 60% Shade - Griffin, Georgia 2020-2022

| | Turf Quality (1-9) | | |
|---|---|---|---|
| Entry | Aug. 18, 2021 | Aug. 17, 2022 | 2-Yr. Avg. |
| Platinum | 4.10 | 4.27 | 4.18 |
| SeaDwarf ™ | 4.83 | **6.33** | **5.58** |
| SeaStar ® | 3.60 | 4.93 | 4.27 |
| 'UGP 73' | **5.83*** | 5.70 | **5.77** |
| Test Average (30 entries) | 4.18 | 5.18 | 4.68 |

*Means in the top statistical group are bolded

TABLE 11

SCRI Greenhouse Salt Trial Seashore Paspalum - 2015 - Griffin, GA - Final Data at 45 dS

| SCRI Entry | Visual Quality (1-9) | Visual Quality (% of control) | Visual Quality (% reduction) | Green Cover (%) | Total Biomass (grams) |
|---|---|---|---|---|---|
| SeaIsle 1 | 3.4 | **55.0** | **45.0** | **21.9** | **2.18** |
| SeaStar ® | **4.1*** | **58.3** | **41.7** | **20.9** | **2.44** |
| 'UGP 73' | **5.0** | **57.9** | **42.1** | **31.1** | **2.35** |
| Test Avg. (9 entries) | 4.2 | 57.1 | 42.9 | 24.7 | 2.32 |

*Means in the top statistical group are bolded

TABLE 12

Summary of 2020 Advanced Seashore Trial - Fairway (0.625 inch h.o.c.) - Griffin, GA

| Entry | Cover Yr 1 (%) | Turf Quality (1-9) | Color (1-9) | NDVI (0-1) | Dollar Spot (%) |
|---|---|---|---|---|---|
| Platinum | **93.3** | 7.2 | 7.3 | 0.71 | **1.0** |
| SeaDwarf ™ | **86.7** | 6.8 | 7.6 | 0.70 | **3.0** |
| SeaStar ® | **90.0** | 7.1 | 7.9 | 0.71 | 15.0 |
| 'UGP 73' | **91.7** | **7.6** | **8.7** | **0.77** | **1.0** |
| Test Average (30 entries) | 80.9 | 7.3 | 7.9 | 0.70 | 4.5 |

*Means in the top statistical group are bolded

TABLE 13

Summary of 2020 Advanced Seashore Trial - Greens Height (0.125 inch h.o.c) - Griffin, GA

| Entry | Establishment Cover (%) | Green up (1-9) | Turf Quality (1-9) | Color (1-9) | Fall Color (1-9) |
|---|---|---|---|---|---|
| SeaDwarf ™ | **76.2*** | **8.2** | 6.8 | 6.0 | 6.4 |
| SeaIsle 2000 | 45.6 | **8.4** | **7.9** | **6.7** | **7.4** |
| SeaStar ® | **71.2** | **8.6** | **7.0** | 6.6 | **7.6** |
| Platinum | 60.0 | **8.5** | **7.1** | **6.8** | **7.5** |
| 'UGP 73' | 56.2 | **8.5** | **7.1** | **7.2** | 5.8 |
| Test Mean 28 entries | 69.3 | 7.7 | 6.6 | 6.42 | 6.0 |

| Entry | Winter Color (1-9) | Seed Heads (1-9) | Dollar Spot (%) | NDVI[1] (0-1) | Stimp (ft.) |
|---|---|---|---|---|---|
| SeaDwarf ™ | **6.4** | 6.5 | **5.1** | 0.64 | **7.2** |
| SeaIsle 2000 | **6.8** | 8.3 | **4.4** | 0.63 | **6.9** |
| SeaStar ® | **7.6** | 7.1 | **3.9** | 0.63 | **7.0** |
| Platinum | **7.4** | 3.1 | **4.8** | 0.64 | **6.9** |
| 'UGP 73' | 5.8 | 8.1 | **3.9** | 0.65 | **7.1** |
| Test Mean 28 entries | 5.4 | 7.4 | 5.5 | 0.62 | 7.0 |

[1]Normalized difference vegetative index is a measure of canopy density and color.
*Means in the top statistical group are bolded.

TABLE 14

Comparison of botanical characteristics of seashore paspalum cultivars.

| | Platinum TE' | Sea-Dwarf ™' | Sea-Star ®' | Sea-Isle 1' | 'UGP 73'' |
|---|---|---|---|---|---|
| Characteristics of Flowering Tillers | | | | | |
| Length of peduncle (mm) | | | | | |
| Mean | 3.3 c[1] | 6.8 b | 4.2 bc | 9.5 a | 9.6 a |
| Std. Dev. | 2.8 | 1.7 | 2.7 | 2.9 | 5.1 |
| Diameter of peduncle (mm) | | | | | |
| Mean | 0.5 bc | 0.5 c | 0.5 c | 0.6 ab | 0.6 a |
| Std. Dev. | 0.1 | 0.1 | 0.1 | 0.1 | 0.1 |
| Length of longest spike (mm) | | | | | |
| Mean | 25.2 abc | 16.4 d | 21.5 c | 26.5 ab | 23.7 bc |
| Std. Dev. | 4 | 5 | 4 | 4.6 | 4.5 |
| Number of spikes per inflourescent | | | | | |
| Mean | 2 | 2 | 2 | 2 | 2 |
| Std. Dev. | 0 | 0 | 0 | 0 | 0 |
| Maxiumum number of spikes per inflourescent | | | | | |
| Mean | 2 | 2 | 2 | 2 | 2 |
| Std. Dev. | 0 | 0 | 0 | 0 | 0 |
| Length of spike branch from flag leaf (mm) | | | | | |
| Mean | 8.6 ab | 6.2 bcd | 5.3 cd | 7.8 abc | 8.9 ab |
| Std. Dev. | 2.2 | 2.3 | 2.5 | 3.7 | 5.20 |

TABLE 14-continued

Comparison of botanical characteristics of seashore paspalum cultivars.

| | Plati-num TE' | Sea-Dwarf ™' | Sea-Star ®' | Sea-Isle 1' | 'UGP 73" |
|---|---|---|---|---|---|
| Florets per spike | | | | | |
| Mean | 16.2 bc | 15 c | 19.3 ab | 19.9 a | 15.7 c |
| Std. Dev. | 3 | 4 | 2.5 | 3.4 | 3.2 |
| Length of blade on flag leaf (mm) | | | | | |
| Mean | 18.9 a | 9.1 bc | 9 bc | 10.2 bc | 6 c |
| Std. Dev. | 4.9 | 2 | 2.4 | 3.5 | 2 |
| Width of blade on flag leaf (mm) | | | | | |
| Mean | 0.8 ab | 0.7 ab | 0.8 ab | 0.6 b | 0.9 a |
| Std. Dev. | 0.2 | 0.3 | 0.2 | 0.3 | 0.2 |
| Length of sheath on flag leaf (mm) | | | | | |
| Mean | 45.2 a | 26.7 cd | 29.6 bc | 44.5 a | 33.3 b |
| Std. Dev. | 5.5 | 6.8 | 6.5 | 8 | 4.3 |
| Length/width ratio of flag leaf blade (mm) | | | | | |
| Mean | 25.2 a | 17.1 bc | 12.3 cd | 19.0 abc | 6.9 d |
| Std. Dev. | 5.1 | 11.3 | 3.7 | 9.4 | 2.3 |
| Length of blade on 4th leaf (mm) | | | | | |
| Mean | 48.2 bc | 38.1 d | 43 cd | 56 ab | 37.4 d |
| S.D | 4.1 | 6.4 | 7.8 | 11.9 | 11.5 |
| Width of blade on 4th leaf (mm) | | | | | |
| Mean | 3.1 ab | 2.2 c | 3.2 a | 3 ab | 3.1 ab |
| Std. Dev. | 0.5 | 0.7 | 0.5 | 0.3 | 0.6 |
| Length of sheath on 4th leaf (mm) | | | | | |
| Mean | 14.6 abc | 12.3 c | 16.1 ab | 16.9 a | 14.1 bc |
| Std. Dev. | 2.1 | 3.5 | 1.6 | 2.5 | 2.6 |
| Length of 4th internode (mm) | | | | | |
| Mean | 11.6 a | 5.3 c | 7.8 cb | 11.3 ab | 11.3 ab |
| Std. Dev. | 3.1 | 1.6 | 2.1 | 2.8 | 4.1 |
| Characteristics of Stolons | | | | | |
| Length of 4th internode (mm) | | | | | |
| Mean | 17.8 a | 12.1 b | 11.5 b | 14 b | 13.8 b |
| Std. Dev. | 4.8 | 2.3 | 1.5 | 3.3 | 4.1 |
| Diameter of 4th internode (mm) | | | | | |
| Mean | 2.1 a | 1.4 cd | 1.5 cd | 1.6 bc | 1.6 b |
| Std. Dev. | 0.2 | 0.2 | 0.2 | 0.2 | 0.2 |

TABLE 14-continued

Comparison of botanical characteristics of seashore paspalum cultivars.

| | Plati-num TE' | Sea-Dwarf ™' | Sea-Star ®' | Sea-Isle 1' | 'UGP 73" |
|---|---|---|---|---|---|
| Length of 4th leaf blade (mm) | | | | | |
| Mean | 6.6 b | 4.3 bc | 4.7 bc | 9.2 a | 6.7 ab |
| Std. Dev. | 1.7 | 1.3 | 0.6 | 3.6 | 3.7 |
| Width of 4th leaf blade (mm) | | | | | |
| Mean | 2.6 a | 1.3 cd | 1.6 bc | 2.1 ab | 2.6 a |
| Std. Dev. | 0.6 | 0.5 | 0.4 | 0.7 | 0.7 |
| Length/width ratio of 4th leaf blade (mm) | | | | | |
| Mean | 2.6 c | 3.7 bc | 3.2 c | 4.9 a | 2.5 c |
| Std. Dev. | 0.8 | 1.6 | 0.8 | 2.1 | 0.9 |
| Length of leaf sheath on 4th node (mm) | | | | | |
| Mean | 8.3 a | 4.8 c | 6.6 b | 8.9 a | 8.6 a |
| Std. Dev. | 1.2 | 1 | 0.7 | 1.9 | 1 |
| Other Characteristics | | | | | |
| Culm height (cm) | | | | | |
| Mean | 18.5 b | 5.5 e | 11.4 c | 22.3 a | 16.4 b |
| Std. Dev. | 2.9 | 1.9 | 1.4 | 3.3 | 2 |
| Seed head height (cm) | | | | | |
| Mean | 17.7 a | 2.9 d | 6.9 c | 17.4 a | 4.8 d |
| Std. Dev. | 2.3 | 0.9 | 0.9 | 2.7 | 1.9 |
| Color of upper leaf surface | | | | | |
| | 138 B[2] | 137 D | 137 D | 137 D | 137 B |
| Color of lower leaf surface | | | | | |
| | 137 A | 137 C | 137 C | 137 C | 137 C |
| Stolon Color | | | | | |
| | 146 C | 146 B | 146 D | 146 D | 146 D |
| Anther Color | | | | | |
| | 83 B | 83 B | 83 A | 83 A | 83 A |
| Stigma Color | | | | | |
| | 86 A | 86 A | 86 B | 86 B | 86 A |

[1]Means within a row followed by the same letter are not considered statistically different according to Fisher's protected LSD at $\alpha = 0.05$.
[2]Based on color codes of The Royal Horticultural Society Colour Chart.

What is claimed is:

1. A new and distinct cultivar of *Paspalum vaginatum* Swartz plant named 'UGP 73' as illustrated and described herein.

* * * * *